(12) United States Patent
Mezei et al.

(10) Patent No.: US 8,394,993 B2
(45) Date of Patent: Mar. 12, 2013

(54) PROCESS FOR THE PREPARATION OF PHARMACEUTICAL INTERMEDIATES

(75) Inventors: Tibor Mezei, Budapest (HU); Gyula Lukács, Budapest (HU); Enikó Molnár, Erd (HU); József Barkóczy, Budapest (HU); Balázs Volk, Budapest (HU); Márta Porcs-Makkay, Pomáz (HU); János Szulágyi, Budapest (HU); Mária Vajjon, Budapest (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 189 days.

(21) Appl. No.: 12/742,484

(22) PCT Filed: Nov. 27, 2008

(86) PCT No.: PCT/HU2008/000138
§ 371 (c)(1),
(2), (4) Date: Jul. 8, 2010

(87) PCT Pub. No.: WO2009/068923
PCT Pub. Date: Jun. 4, 2009

(65) Prior Publication Data
US 2010/0274020 A1    Oct. 28, 2010

(30) Foreign Application Priority Data
Nov. 27, 2007   (HU) ..................... 0700756

(51) Int. Cl.
*C07D 495/04*    (2006.01)
*C07C 45/45*    (2006.01)
*C07C 45/65*    (2006.01)

(52) U.S. Cl. .................. 568/322; 568/323; 546/114

(58) Field of Classification Search .................. 568/323, 568/322; 546/114
See application file for complete search history.

(56) References Cited

U.S. PATENT DOCUMENTS
5,436,242 A    7/1995 Koike et al.

OTHER PUBLICATIONS

See Bernstein, J. et. al. "The Preparation and Properties of Some Substituted Benzyl Fluorides" Journal of the American Chemical Society 1948 70, 2310-2314.*
Yu, S.H et. al. "Preparation of Alkylmagnesium Fluorides" Journal of Organic Chemistry 1971, 56, 2123-2128.*
Shin-ya Tosaki et al; Strategy for enantio- and . . . ; Chem. Eur. J. 2004, 10, 1527-1544; XP002531964.
Robert Dillard et al; Indole inhibitors of human . . . ; J. Med. Chem. 1996, 39, 5119-5136; XP 002046054.
Alexandru Razus et al; Synthesis of para-Substituted . . . ; Revue Roumaine de Chimie, 1984, 29, 719-725; XP009118025.
Comptes Rendus Hebdomadaires des Seances de . . . ; 1926, 182, 1393-1395; XP009118022.

* cited by examiner

*Primary Examiner* — David K O'Dell
(74) *Attorney, Agent, or Firm* — Jonathan Myers; Andrew Wilford

(57) ABSTRACT

The invention relates to a process for the preparation of cyclopropyl benzyl ketone compounds of formula (II) wherein $R^1$ represents fluorine or chlorine atom or $C_{1-4}$ alkoxy group, by the reaction of a Grignard reagent, obtained from the reaction of compound of formula (V), wherein X represents chlorine or fluorine atom, with the compound of formula (IV), wherein $R_2$ represents $C_{1-4}$ alkyl group, having a straight or branched chain. The process can be applied preferably on industrial scale. Compound of formula (II), wherein R represents a fluorine atom in position 2 is an intermediate of the preparation process of prasugrel, which is a platelet inhibitor used in the therapy.

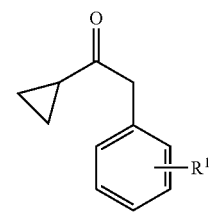

II

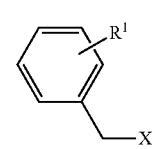

V

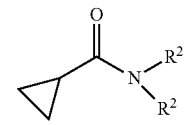

IV

11 Claims, 1 Drawing Sheet

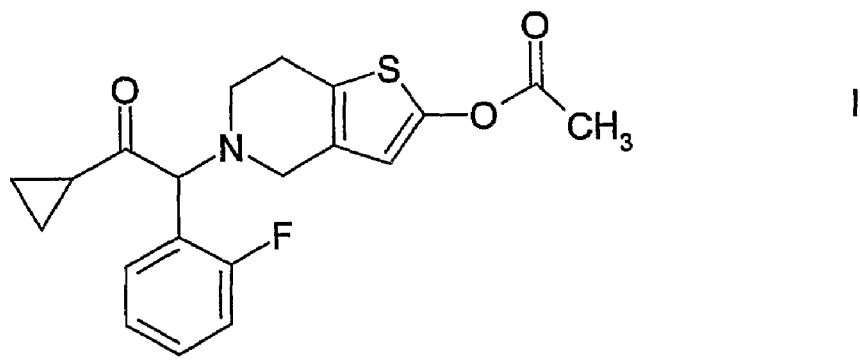
I
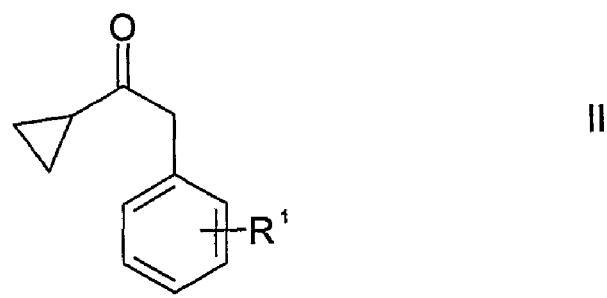
II
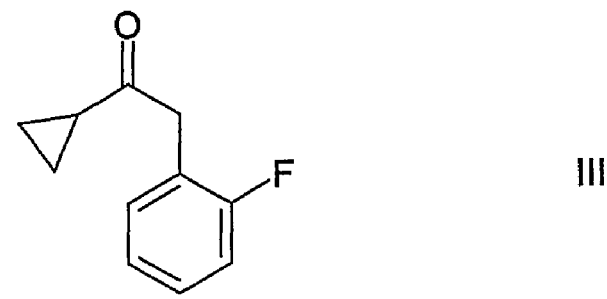
III
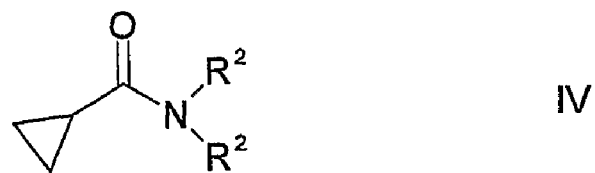
IV
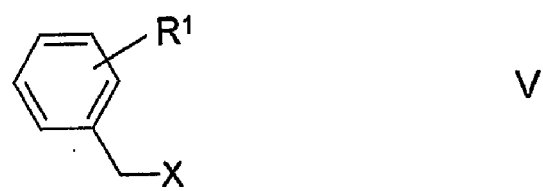
V

PROCESS FOR THE PREPARATION OF PHARMACEUTICAL INTERMEDIATES

CROSS REFERENCE TO RELATED APPLICATIONS

This application is the US national Phase of PCT/HU 2008/000138 filed 27 Nov. 2008 and claiming the benefit of the priority date of Hungarian Patent Application HU P 0700756 filed 27 Nov. 2007.

FIELD OF THE INVENTION

The invention relates to a process for the preparation of cyclopropyl benzyl ketone compounds of general formula (II) by the reaction of Grignard reagent prepared from compounds of formula (V) and cyclopropanecarboxylic acid dialkylamide compounds of formula (IV) which can be applied preferably on industrial scale.

BACKGROUND OF THE INVENTION

Cyclopropyl benzyl ketone compounds of general formula (II) are important starting compounds of tetrahydro thienopyridine derivatives, which are used in the pharmaceutical therapy. One of the most important representatives of tetrahydro thienopyridine derivatives is compound of formula (I), namely 5-[2-cyclopropyl-1-(2-fluorophenyl)-2-oxoethyl]-4,5,6,7-tetrahydrothieno[3,2-c]-pyridin-2-yl acetate, having the international non-proprietary name prasugrel, used for the prevention and treatment of thrombosis and thromboembolism.

The platelet inhibitor prasugrel, its derivatives, and the process for their preparation was described for the first time by Hungarian Patent No. 218 785 and Hungarian Patent No. 211 876. The object of the present invention relates to a process for the preparation of cyclopropyl benzyl ketone compounds of formula (II) in high purity, constituting a very important structural part of the above mentioned compounds. The process is very well-applicable on industrial scale.

In the preparation process of prasugrel, and the effective platelet inhibitor compounds having a similar chemical structure, the key intermediates are the ketone compounds of general formula (II), which can have different substituents on the aromatic ring. The most important representatives of these compounds are the halogen substituted derivatives, especially those substituted by chlorine or fluorine atoms. From the literature only a few preparation processes of these derivatives are known which are narrowly applicable on industrial scale.

According to the preparation process described in Hungarian Patent No. 218 785 and Hungarian Patent No. 211 876 cyclopropyl benzyl ketone compounds of formula (II) are prepared by the reaction of 2-fluorobenzyl magnesium bromide or 2-chlorobenzyl magnesium bromide and cyclopropanecarbonitrile. The reaction is carried out at the boiling point of diethyl ether, and the obtained complex is quenched with aqueous ammonium chloride, the product is extracted and purified by column chromatography. The yield of the process is 70% or 69%, respectively.

Hungarian Patent No. 211 876 also describes another process, wherein the compound of 2-fluorobenzyl magnesium halogenide is reacted, instead of cyclopropanecarbonitrile, with an acid chloride, for example cyclobutanecarbonyl chloride. The reaction is carried out at a very low temperature (−70° C.), and the pure product is obtained by extraction and purification by column chromatography. The yield of the process is very low, 39%.

In the above mentioned Grignard reactions for the preparation of compounds of formula (II) it is possible that the ester, nitrile or acid chloride reagents react with two equivalents of the Grignard reagent, instead of one. These reactions reduce the yield of the manufacturing process, and some by-products, containing a hydroxyl group, can be derived from the process.

In the preparation processes described in Hungarian Patents No. 218 785 and 211 876, the Grignard reagents are obtained from bromo derivatives. According to the present invention, in the preparation process of cyclopropyl benzyl ketone compounds of formula (II), the Grignard reagent is obtained from the more suitable and cheaper 2-fluorobenzyl chloride instead of 2-fluorobenzyl bromide. Among the halogen derivatives, the use of chloro derivatives is more economical, because they are cheaper and the applied amount is less, because they have a lower molecular weight than the bromo derivatives.

Preparation processes described in Hungarian Patent No. 211 876 are not suitable for the preparation of a drug on industrial scale, because the purification is carried out by column chromatography and this purification process is not suitable for the preparation of a large quantity of the final product. A large amount of reagents is needed for the purification therefore the process is more expensive and also very pollutive for the environment.

Another disadvantage of the reactions known from the literature is that the carboxylic acid derivatives, namely the acid chlorides and the anhydrides—see the description of Hungarian Patent No. 211 876—react with benzylmagnesium bromide at a very low temperature, at −70-−50° C. Therefore these processes—beyond the difficulties caused by the purification of column chromatography—are hardly applicable on an industrial scale and are energy-consuming and expensive reactions.

In U.S. Pat. No. 5,874,581 a process is described for the preparation of compound of formula (III), wherein two equivalents of 2-propyl magnesium chloride are reacted with 2-fluoroacetic acid in tetrahydrofuran, at the boiling point of the solvent. The obtained complex is reacted at a temperature of 5° C. with ethyl or methyl cyclopropanecarboxylate. The reaction mixture is stirred for three hours and hydrochloric acid is added, then the mixture is neutralized, extracted, evaporated, and finally the fractions are obtained in vacuo.

The disadvantage of the preparation process described in U.S. Pat. No. 5,874,581 is that very expensive starting materials and more than two equivalents of the Grignard reagent are used in the synthesis. The yield of the reaction is 56%, the purity of the final product is not mentioned.

OBJECTS OF THE INVENTION

The aim of the present invention is to avoid the disadvantages of the above processes and to develop an economical, simple preparation process in a good yield, which avoids the purification by column chromatography and which can be applied advantageously on an industrial scale.

The above mentioned aims are reached by the preparation process of the present invention.

SUMMARY OF THE INVENTION

The present invention is a process for the preparation of compounds of the formula (I).

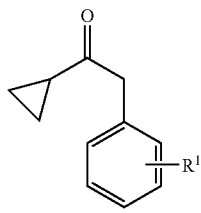

II wherein R¹ represents fluorine, chlorine atom or $C_{1-4}$ alkoxy group, wherein the Grignard reagent, obtained from the compound of general formula (V),

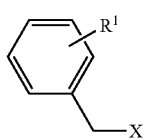

V wherein X represents chlorine or fluorine atom, is reacted with the compound of general formula (IV),

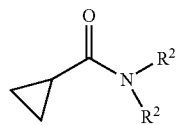

IV wherein $R_2$ represents $C_{1-4}$ alkyl group, having a straight or branched chain.

According to the present invention for the preparation of the Grignard reagent preferably a compound of formula (V),

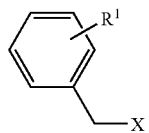

wherein X represents a chlorine atom, and 1.0-1.5 mol equivalents, preferably 1.0-1.3 mol equivalents of magnesium are used, calculated on the compound of formula (V), thereafter the Grignard reagent is reacted with 0.7-1.1 mol equivalents of compound of formula (IV).

The $C_{1-4}$ alkoxy group herein means such a functional straight or branched alkyl group having 1-4 carbon atoms which is bound to an oxygen atom.

In the process among the dimethylamide derivatives preferably a compound of formula (IV) is used when R² preferably represents a methyl group.

According to the present invention the reaction is carried out in an ether type solvent, e.g. in diethyl ether, in tert-butyl methyl ether, in diisopropyl ether, in dibutyl ether, in tetrahydrofuran or in dioxane, preferably the reaction is carried out in diethyl ether, in tert-butyl methyl ether or in diisopropyl ether, at a temperature between 20 and 100° C., preferably at the boiling point of the ether type solvent.

BRIEF DESCRIPTION OF THE DRAWINGS

The sole FIGURE in this application is a formula sheet listing the structural formulae for the compounds of the Formulae I, II, III, IV and V.

DETAILED DESCRIPTION OF THE INVENTION

The reaction of Grignard reagents with a carboxylic acid derivative is a well-known and often used method for the preparation of ketone derivatives. The Grignard reaction proceeds via a radical mechanism, therefore during the reaction a lot of by-products are prepared, for example dibenzyl derivatives and usually some other products (toluene, alcohol derivatives etc.) are also obtained by reduction. According to the state of the art, there is a possibility that the ester, nitrile or acid chloride reagents react with two equivalents of Grignard reagent instead of one. This significantly reduces the yield of the reaction and hydroxyl-group containing by-products are prepared.

It was surprisingly found that when a cyclopropanecarboxylic acid dimethylamide of formula (IV), wherein R² represents a methyl group, is reacted with 2-fluorobenzylmagnesium chloride, the amount of the side products arising from the reaction with the second Grignard reagent, is significantly lower. The reaction is carried out at room temperature and compound of formula (III) can be obtained in almost quantitative yield.

According to the present invention the Grignard reagent is prepared from the cheaper 2-fluorobenzyl chloride derivative, instead of the bromine derivative and this reagent provides a good yield in the reaction of cyclopropanecarboxylic acid dialkylamides. According to our experiments with other derivatives of cyclopropanecarboxylic acid, the product of the reaction can be obtained only in a yield of 5-17%. At the reproduction of the reaction of Hungarian Patents No. 218 785 and 211 876 (described in example 10), wherein the 2-fluorobenzyl magnesium bromide reagent was replaced by 2-fluorobenzyl magnesium chloride, it was found that reacting the Grignard reagent in ether with cyclopropanecarbonyl chloride at a temperature of −70° C. only 5% of the product was obtained by GC/MS measurements. In example 11 reacting with cyclopropanecarbonitrile reagent under the same conditions but at a higher temperature, only 16.5% product was obtained, beside a lot of different side products Accordingly another advantage of our process preparing a compound of formula (II) from cyclopropanecarboxylic acid dialkylamide of formula (IV) that the Grignard reagent is prepared from the cheaper benzyl chloride derivative. Preparing the Grignard reagent from the suitable benzyl chloride of formula (V), reacted on . . . with this cyclopropanecarboxylic acid dialkylamide, the yield of the reactions is doubled when compared to the reaction carried out with the bromo derivative of the Grignard reagent.

If the Grignard reagent is obtained from 2-fluorobenzyl chloride, then the highest yield can be obtained with cyclopropanecarboxylic acid dimethylamide among all cyclopropanecarboxylic acid dialkylamide derivatives of formula (IV).

We have studied, whether the most suitable cyclopropanecarboxylic acid dimethylamides with different substituents on the aromatic ring, have a similar reaction with the benzyl magnesium chlorides. It was found that the reaction could be carried out in a high yield with all examined substituted benzyl chlorides of general formula (V) [X═Cl, R²═F, Cl or OMe], independently from the position (ortho, meta or para) of the substituent.

The yield of the preparation process of our invention for the synthesis of compounds of general formula (II) is around 80%.

The reaction is carried out in an ether type solvent. Such ether type solvents can be the following: diethyl ether, tert-butyl methyl ether, diisopropyl ether, dibutyl ether, tetrahydrofuran or dioxane. It was found that the most suitable solvent is diethyl ether.

The reaction can also be easily carried out in tent-butyl methyl ether, diisopropyl ether and dibutyl ether which are less inflammable.

The process of our invention can be simply carried out on a plant scale, can be easily scaled up and does not need any special conditions or apparatus. The preparation process of the present invention can be optimally carried out on a plant scale, the conditions of the reaction are not extreme. Another advantage of our invention is that the use of toxic, environmentally dangerous, corrosive reagents is avoided together with technologies needing large amounts of solvents (for example column chromatography) or a very low temperature (e.g. −78° C.).

The end product of our invention, compound of formula (III), which is in the scope of general formula (II), is an important starting compound of the derivatives of the pharmaceutically applicable tetrahydro thienopyridine derivatives.

Prasugrel, compound of the formula (I) is prepared from compound of formula (III), synthesised according to the process of the present invention, by the chlorination or bromination of compound of formula (III) and the obtained compound is then reacted with 4,5,6,7-tetrahydro-thieno[2,3-c]pyridine, according to the manufacturing process described in Hungarian Patent No. HU 211 876. In position 2 of the thiophene ring, the oxo group is obtained by the methods known from the art and prasugrel of formula (I) is finally obtained by O-acetylation under basic conditions and, if desired, it is converted to its acid additional salts.

EXAMPLES

The invention is further elucidated by means of the following Examples without restricting the scope of the present invention to the Examples.

Example 1

Preparation of Cyclopropanecarboxylic Acid Dimethylamide [Compound of Formula (IV), $R^2$=Me]

In a 250 ml round-bottomed flask, thionyl chloride (110 ml, 1.5 mol) and dimethylformamide (1.5 ml) are added and under stirring at 25-30° C., cyclopropanecarbonyl chloride (90 ml, 1.14 mol) is added dropwise to the solution over 1.5 hours. The reaction mixture is refluxed for 2 hours, until the cessation of gas formation. Without further preparation and purification the crude acid chloride is added dropwise over 1.5 hours to the mixture of crushed ice (300 g), aqueous sodium hydroxide (300 ml, 40 w/w %) and dimethylamine hydrochloride (186 g, 2.3 mol). The reaction mixture is stirred for 1 hour at 25° C. The obtained product is extracted with dichloromethane (2×200 ml) and the organic layer is dried over magnesium sulfate, distilled and the residue is fractionated in vacuo at a pressure of 10 Hgmm.

| | |
|---|---|
| Boiling point: | 44° C./10 Hgmm |
| Yield: | 104.9 g (81.4%) colourless oil |
| Content (measured by GC): | 98.4% |
| Refractive index: | $[n_D^{20}]$ = 1.4708 |

IR (film): 3529, 3011, 2935, 1645, 1501, 1420, 1337, 1265, 1204, 1140, 1060.
$^1$H-NMR (CDCl$_3$, 500 MHz): 3.18 (s, 3H), 2.97 (s, 3H), 1.75 (m, 1H), 0.96 (m, 2H), 0.75 (m, 2H).
$^{13}$C-NMR (CDCl$_3$, 125 MHz): 173.3, 37.0, 35.7, 10.9, 7.2.

Example 2

Preparation of Cyclopropanecarboxylic Acid Diethylamide [Compound of Formula (IV), $R^2$=Et]

The preparation process is carried out according to example 1, with the difference that instead of dimethylamine hydrochloride diethylamine hydrochloride (252.1 g, 2.3 mol) is added to the reaction mixture.

| | |
|---|---|
| Boiling point: | 54° C./5 Hgmm |
| Yield: | 54.5 g (33.9%) colourless oil |
| Content (measured by GC): | 97.4% |
| Refractive index: | $[n_D^{20}]$ = 1.4593 |

Example 3

Preparation of Cyclopropanecarboxylic Acid Diisopropylamide [Compound of Formula (IV), $R^2$=i-Pr]

The preparation process is carried out according to example 1, with the difference that instead of dimethylamine hydrochloride diisopropylamine hydrochloride (252.1 g, 2.3 mol) is added to the reaction mixture.

| | |
|---|---|
| Boiling point: | 60° C./2.5 Hgmm |
| Yield: | 71.5 g (37.1%) colourless oil |
| Content (measured by GC): | 98.2% |
| Boiling point: | 18-20° C. |

Example 4

Preparation of Cyclopropyl 2-Fluorobenzyl Ketone [Compound of Formula (III)]

A 1000 ml round-bottomed flask is filled with magnesium (10.7 g, 0.44 mol). Iodine (0.2 g) is sublimated to the magnesium, then diethyl ether (240 ml) is added and under reflux, a solution of 2-fluorobenzyl chloride (47.8 ml, 0.4 mol) and diethyl ether (80 ml) is added to the reaction mixture. The mixture is refluxed for 2 hours and at this temperature a solution of cyclopropanecarboxylic acid dimethylamide (36.2 g, 0.32 mol), prepared according to example 1, and tetrahydrofuran (200 ml) are added. The reaction mixture is stirred for half an hour and under cooling aqueous hydrogen chloride (160 ml, 1:1) is added dropwise to the mixture. The organic layer is dried and the residue is fractionated in vacuo.

| Boiling point: | 61° C./0.2 Hgmm |
| --- | --- |
| Yield: | 46.6 g (79.8%) colourless oil |
| Content (measured by GC): | 97.7% |
| Refractive index: | $[n_D^{20}] = 1.5169$ |

IR (film): 3010, 1704, 1587, 1494, 1457, 1384, 1234, 1072, 1025.

$^1$H-NMR (CDCl$_3$, 500 MHz): 7.25 (dd, 1H), 7.20 (t, 1H), 7.10 (t, 1H), 7.06 (t, 1H), 3.87 (s, 2H), 1.99 (m, 1H), 1.06 (m, 2H), 0.87 (m, 2H).

$^{13}$C-NMR (CDCl$_3$, 125 MHz): 206.9 (d, J=1.0 Hz), 161.0 (d, J=246.1 Hz), 131.6 (d, J=4.4 Hz), 128.8 (d, J=8.3 Hz), 124.1 (d, J=3.4 Hz), 121.8 (d, J=16.6 Hz), 115.3 (d, J=21.5 Hz), 43.5 (d, J=2.4 Hz), 20.0 (d, J=1.0 Hz), 11.2.

Example 5

Preparation of Cyclopropyl 2-Fluorobenzyl Ketone [Compound of Formula (III)]

A 1000 ml round-bottomed flask is filled with magnesium (10.7 g, 0.44 mol). Iodine (0.2 g) is sublimated to the magnesium, then tert-butyl methyl ether (240 ml) is added and under boiling, a solution of 2-fluorobenzyl chloride (47.8 ml, 0.4 mol) and tert-butyl methyl ether (80 ml) is added to the reaction mixture. The mixture is refluxed for 2 hours and at this temperature a solution of cyclopropanecarboxylic acid dimethylamide (36.2 g, 0.32 mol), prepared according to example 1, and tetrahydrofuran (200 ml) are added. The reaction mixture is stirred for half an hour and under cooling aqueous hydrogen chloride (160 ml, 1:1) is added dropwise to the mixture. The organic layer is dried and the residue is fractionated in vacuo.

| Yield: | 35.6 g (60.9%) colourless oil |
| --- | --- |
| Content (measured by GC): | 97.7% |
| Refractive index: | $[n_D^{20}] = 1.5167$ |

Example 6

Preparation of Cyclopropyl-2-Fluorobenzyl-Ketone [Compound of Formula (III)]

A 250 ml round-bottomed flask is filled with magnesium (2.67 g, 0.11 mol) and iodine (0.1 g) is sublimated to the magnesium, then diethyl ether (60 ml) is added and under boiling a solution of 2-fluoro-benzyl chloride (11.9 ml, 0.1 mol) and diethyl ether (20 ml) is added to the reaction mixture. The mixture is boiled for 2 hours and at this temperature a solution of cyclopropanecarboxylic acid diethylamide (11.3 g, 80 mmol), prepared according to example 2, and tetrahydrofuran (50 ml) are added. The reaction mixture is stirred for half an hour and under cooling aqueous hydrogen chloride (40 ml, 1:1) is added dropwise to the mixture. The organic phase is dried and the residue is fractionated in vacuo.

| Yield: | 6.94 g (48.7%) colourless oil |
| --- | --- |
| Boiling point: | 60° C./0.2 Hgmm |
| Content (measured by GC): | 96.9% |
| Refractive index: | $[n_D^{20}] = 1.5165$ |

Example 7

Preparation of Cyclopropyl-2-Fluorobenzyl-Ketone [Compound of Formula (III)]

The preparation process is carried out according to example 6, with the difference that the Grignard reagent is prepared according to example 3, with a solution of cyclopropanecarboxylic acid diisopropylamide (13.5 g, 80 mmol) and tetrahydrofuran (50 ml), instead of cyclopropanecarboxylic acid-diethylamide. The reaction mixture is stirred for two hours and under cooling aqueous hydrogen chloride (40 ml, 1:1) is added dropwise to the mixture. The organic phase is dried and the residue is fractionated in vacuo by microdistillation.

| Yield: | 3.2 g (22.5%) colourless oil |
| --- | --- |
| Content (measured by GC): | 90.9% |
| Refractive index: | $[n_D^{20}] = 1.5169$ |

Example 8

Preparation of Cyclopropyl-4-Chlorobenzyl-Ketone [Compound of Formula (II), R$^1$=4-Cl]

A 500 ml round-bottomed flask is filled with magnesium (5.8 g, 0.24 mol) and iodine (0.1 g) is sublimated to the magnesium, then diethyl ether (120 ml) is added and under boiling a solution of 4-chloro benzyl chloride (32.2 g, 0.20 mol) and diethyl ether (40 ml) is added to the reaction mixture. The mixture is boiled for 1 hour and at this temperature a solution of cyclopropanecarboxylic acid dimethylamide (18.1 g, 0.16 mol) and tetrahydrofuran (80 ml) are added. The reaction mixture is stirred for half an hour and under cooling aqueous hydrogen chloride (80 ml, 1:1) is added dropwise to the mixture. The organic layer is dried and the residue (32 g) is fractionated in vacuo.

| Boiling point: | 96° C./0.4 Hgmm | | |
| --- | --- | --- | --- |
| Yield: | 25.2 g colourless oil (76.0%). | | |
| Content (measured by GC): | 97.2%, crystallized from n-hexane. | | |
| Boiling point: | 38-40° C., white crystals | | |
| Analysis of C$_{11}$H$_{11}$ClO (194.7): | | | |
| Calculated: | C 67.87 | H 5.70 | Cl 18.21 |
| Found: | C 67.41 | H 5.72 | Cl 17.95 |

IR (KBr): 3442, 3011, 1693, 1492, 1378, 1073, 1015.

$^1$H-NMR (CDCl$_3$, 500 MHz): 7.29 (d, 2H, J=8.2 Hz), 7.15 (d, 2H, J=8.2 Hz), 3.80 (s, 2H), 1.95 (m, 1H), 1.04 (m, 2H), 0.87 (m, 2H).

$^{13}$C-NMR (CDCl$_3$, 125 MHz): 207.7, 132.8, 132.8, 130.8, 128.7, 49.7, 20.2, 11.4.

Example 9

Preparation of Cyclopropyl 3-Methoxybenzyl Ketone [Compound of Formula (II), R$^1$=3-MeO]

A 250 ml round-bottomed flask is filled with magnesium (4.9 g, 0.20 mol) and iodine (0.1 g) is sublimated to the magnesium, then diethyl ether (100 ml) is added and under boiling a solution of 3-methoxybenzyl chloride (11.9 ml, 0.1 mol) and diethyl ether (40 ml) are added to the reaction mixture. The mixture is boiled for one hour and at this temperature a solution of cyclopropanecarboxylic acid dimethylamide (16.6 g, 0.15 mol) and tetrahydrofuran (70 ml) are added. The reaction mixture is stirred for half an hour and under cooling aqueous hydrogen chloride (80 ml, 1:1) is added dropwise to the mixture. The organic layer is dried and the residue (32 g) is fractionated in vacuo.

| Yield: | 20.6 g (72.2%) colourless oil |
|---|---|
| Boiling point: | 103° C./0.3 Hgmm |
| Refractive index: | $[n_D^{20}] = 1.5369$ |
| Analysis of $C_{12}H_{14}O_2$ (190.2): | |
| Calculated: | C 75.76  H 7.42 |
| Found: | C 75.23  H 7.51 |

IR (film): 3539, 3008, 2940, 2836, 1695, 1600, 1491, 1438, 1491, 1454, 1383, 1259, 1151, 1071.

$^1$H-NMR (CDCl$_3$, 200 MHz): 7.23 (t, 1H), 6.82 (m, 1H), 6.80 (m, 2H), 3.77 (m, 5H), 1.96 (m, 1H), 1.02 (m, 2H), 0.85 (m, 2H).

Example 10

Preparation of Cyclopropyl 2-Fluorobenzyl Ketone
[Compound of Formula (III)]

A 250 ml round-bottomed flask is filled with magnesium (2.67 g, 0.11 mol) and iodine (0.1 g) is sublimated to the magnesium, then diethyl ether (60 ml) is added and under boiling a solution of 2-fluor benzyl chloride (11.9 ml, 0.1 mol) and diethyl ether (20 ml) is added to the reaction mixture. The mixture is boiled for two hours, then cooled to −70° C. and a solution of cyclopropanecarbonyl chloride (8.36 g, 80 mmol 1) and tetrahydrofuran (50 ml) are added, and the reaction mixture is left to warm to room temperature.

A sample was taken from the reaction mixture and it was washed with aqueous ammonium chloride and examined with GC/MS measurements. The content of the reaction mixture was the following:

| 11.5% | cyclopropanecarboxylic acid |
|---|---|
| 10.8% | 2-fluorobenzyl alcohol, |
| 25.2% | 2-fluorotoluene, |
| 4.8% | compound of formula (III). |

Example 11

Preparation of Cyclopropyl 2-Fluorobenzyl Ketone
[Compound of Formula (III)]

A 250 ml round-bottomed flask is filled with magnesium (2.67 g, 0.11 mol) and iodine (0.1 g) is sublimated to the magnesium, then diethyl ether (60 ml) is added and under boiling a solution of 2-fluor benzyl chloride (11.9 ml, 0.1 mol) and diethyl ether (20 ml) is added to the reaction mixture. The mixture is boiled for two hours, then cooled to −50° C. and a solution of cyclopropanecarbonitrile (5.4 g, 80 mmol) and tetrahydrofuran (50 ml) are added, and the reaction mixture is warmed to boiling point and boiled for half an hour.

A sample is taken from the reaction mixture and it is washed with aqueous hydrochloric acid and examined with GC/MS measurements. The content of the reaction mixture was the following:

| 14.6% | 2-fluorotoluene, |
|---|---|
| 24.4% | 2-fluorobenzyl alcohol, |
| 16.5% | compound of formula (III). |

The invention claimed is:

1. A process for preparing a compound of the Formula (II)

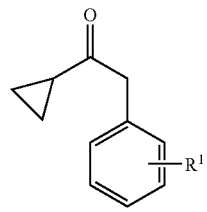

wherein
R$^1$ is fluoro, chloro or C$_1$ to C$_4$ alkoxy, which comprises the step of:
(a) preparing a Grignard reagent by reacting a compound of the Formula (V)

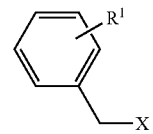

wherein
X is chloro with elemental magnesium; and
(b) reacting the Grignard reagent with a compound of the Formula (IV)

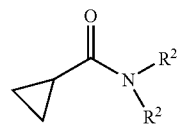

wherein
R$^2$ is C$_1$ to C$_4$ straight or branched chain alkyl to obtain the compound of the Formula (II).

2. The process for preparing the compound of the Formula (II) defined in claim 1 wherein according to step (a) for preparing the Grignard reagent, 1.0 to 1.5 molar equivalents of magnesium are employed per mole of the compound of the Formula (V).

3. The process for preparing the compound of the Formula (II) defined in claim 2 wherein 1.0 to 1.3 molar equivalents of magnesium are employed per mole of the compound of the Formula (V).

4. The process for preparing the compound of the Formula (II) defined in claim 1 wherein according to step (a), the Grignard reagent prepared is 2-fluorobenzyl magnesium chloride.

5. The process for preparing the compound of the Formula (II) defined in claim 1 wherein according to step (b), in the compound of the Formula (IV), R$^2$ is methyl.

6. The process for preparing the compound of the Formula (II) defined in claim 1 wherein according to step (b), one molar equivalent of the Grignard reagent is reacted with 0.7 to 1.1 equivalents of the compound of the Formula (IV).

7. The process for preparing the compound of the Formula (II) defined in claim 1 wherein according to step (b), the reaction is carried out in an ether solvent selected from the group consisting of diethyl ether, tert-butyl methyl ether, diisopropyl ether, dibutyl ether, tetrahydrofuran and dioxane.

8. The process for preparing the compound of the Formula (II) defined in claim 7 wherein the ether solvent is selected from the group consisting of diethyl ether, tert-butyl methyl ether, and diisopropyl ether.

9. The process for preparing the compound of the Formula (II) defined in claim 1 wherein according to step (b) the reaction is carried out at a temperature between 20 to 100° C.

10. The process for preparing the compound of the Formula (II) defined in claim 1 wherein according to step (b) the reaction is carried out at the boiling point of the ether solvent.

11. A process for preparing a compound of the Formula (I)

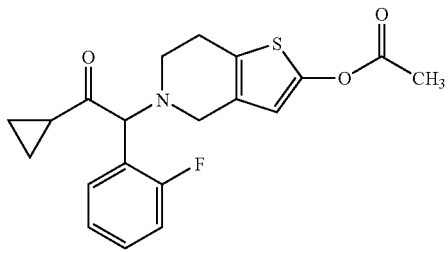 [SMILES: CC(=O)Oc1cc2c(s1)CCN(C(C(=O)C1CC1)c1ccccc1F)C2]

which comprises the steps of:
(a) preparing a Grignard reagent by reacting a compound of the Formula (V)

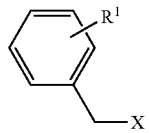

wherein
$R^1$ is 2-fluoro and X is chloro with elemental magnesium;
(b) reacting the Grignard reagent with a compound of the Formula (IV)

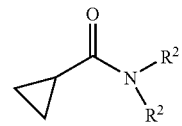

wherein
$R^2$ is $C_1$ to $C_4$ straight or branched chain alkyl to obtain the compound of the Formula (III)

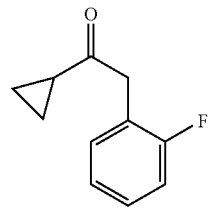 [SMILES: O=C(Cc1ccccc1F)C1CC1]

and,
(c) reacting the compound of the Formula (III) by chlorinating or brominating the compound, and the obtained compound is then reacted with 4,5,6,7-tetrahydro-thieno[2,3-c]pyridine, an oxo substituent is introduced at position 2-, and then the product is O-acetylated under basic conditions to obtain the compound of the Formula (I).

* * * * *

UNITED STATES PATENT AND TRADEMARK OFFICE
CERTIFICATE OF CORRECTION

PATENT NO.       : 8,394,993 B2
APPLICATION NO.  : 12/742484
DATED            : March 12, 2013
INVENTOR(S)      : Mezei et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 232 days.

Signed and Sealed this
First Day of September, 2015

Michelle K. Lee
*Director of the United States Patent and Trademark Office*